United States Patent [19]
Xiong et al.

[11] Patent Number: 5,541,417
[45] Date of Patent: Jul. 30, 1996

[54] QUANTATIVE AGGLUTINATION REACTION ANALYSIS METHOD

[75] Inventors: Yongli H. Xiong, Libertyville; Eric L. Russell, Gurnee, both of Ill.

[73] Assignee: Abbott Laboratories, Abbott Park, Ill.

[21] Appl. No.: 443,920

[22] Filed: May 18, 1995

[51] Int. Cl.$^6$ .................................................. G01N 33/80
[52] U.S. Cl. ...................... 250/559.05; 250/576; 382/128
[58] Field of Search .............................. 250/559.05, 576; 356/335, 246, 39; 382/6, 14; 422/58

[56] References Cited

U.S. PATENT DOCUMENTS

| | | | |
|---|---|---|---|
| 4,436,827 | 3/1984 | Tamagowa | 436/534 |
| 4,465,938 | 8/1984 | Kato et al. | 250/576 |
| 4,466,740 | 8/1984 | Kano et al. | 356/246 |
| 4,554,257 | 11/1985 | Aladjem et al. | 436/519 |
| 4,556,641 | 12/1985 | Kano et al. | 436/165 |
| 4,563,430 | 1/1986 | Kona et al. | 436/164 |
| 4,661,460 | 4/1987 | Sakuma | 436/165 |
| 4,770,855 | 9/1988 | Sakuma | 422/102 |
| 4,806,015 | 2/1989 | Cottingham | 356/335 |
| 5,017,341 | 5/1991 | Takekawa | 422/102 |
| 5,162,234 | 11/1992 | Tanaka et al. | 436/165 |
| 5,188,968 | 2/1993 | Kano et al. | 436/501 |
| 5,192,692 | 3/1993 | Sakai et al. | 436/165 |
| 5,209,904 | 5/1993 | Forney | 422/73 |
| 5,225,350 | 7/1993 | Watanabe et al. | 436/165 |
| 5,238,852 | 8/1993 | Sakai et al. | 436/165 |
| 5,248,479 | 9/1993 | Parsons et al. | 422/58 |
| 5,265,169 | 11/1993 | Ohta et al. | 382/6 |
| 5,270,166 | 12/1993 | Parsons et al. | 435/7.4 |
| 5,283,178 | 2/1994 | Kessler et al. | 435/7.25 |
| 5,290,517 | 3/1994 | Samuels et al. | 422/58 |
| 5,388,164 | 2/1995 | Yonekawa et al. | 382/6 |
| 5,389,555 | 2/1995 | Watanabe et al. | 436/164 |

FOREIGN PATENT DOCUMENTS

| | | | |
|---|---|---|---|
| 43803/85 | 6/1985 | Australia | G01N 21/82 |
| 0198327A2 | 10/1986 | European Pat. Off. | G01N 33/82 |
| 0583626A2 | 2/1994 | European Pat. Off. | G01N 21/82 |
| 0637744A1 | 2/1995 | European Pat. Off. | G01N 21/82 |
| 3343149A1 | 5/1984 | Germany | G01N 33/48 |
| 4313603A1 | 10/1993 | Germany | G01N 35/00 |
| 2-309232 | 12/1990 | Japan | G01N 21/17 |
| 3-108638 | 5/1991 | Japan | G01N 21/17 |
| 4-120442 | 4/1992 | Japan | G01N 22/00 |
| WO92/22880 | 12/1992 | WIPO | G06K 9/00 |
| WO94/11841 | 5/1994 | WIPO | G06F 15/70 |
| WO94/17212 | 8/1994 | WIPO | C12Q 1/70 |

OTHER PUBLICATIONS

"ANSim User Manual". Science Applications International Corporation, pp. 4/13–4/25.
"ANSim 2.30 Update Information". Science Applications International Corporation, Apr. 28, 1989, p. 1.
"Neural Network Medical Diagnostic Image Investigation Report". Hecht–Nielsen Neurocomputers, Aug. 9, 1989.

*Primary Examiner*—Stephone Allen
*Attorney, Agent, or Firm*—Mark C. Bach

[57] ABSTRACT

Embodiments described herein provide methods of analysis of a reaction, such as an agglutination reaction producing an agglutination pattern, and the like. In one method, an image of the agglutination pattern is captured. The image captured is digitized to form a digital image comprising a pixel. Roughness is measured, reflecting pixel local environment, at each pixel comprising a region of interest of the digital image of the agglutination pattern. At least one of classification and quantification of the image captured of the agglutination pattern is performed based on the measured roughness. In another embodiment, roughness is derived using a shared weights neural network approach, the roughness reflecting pixel local environment at each pixel comprising a region of interest of the digital image of the agglutination pattern. At least one of classification and quantification of the image captured of the agglutination pattern is performed based on the derived roughness. In a further embodiment, a feature is derived using a shared weights neural network approach, the feature reflecting pixel local environment at each pixel comprising a region of interest of the digital image of the agglutination pattern. At least one of classification and quantification of the image captured of the agglutination pattern is performed based on the derived feature.

12 Claims, 5 Drawing Sheets

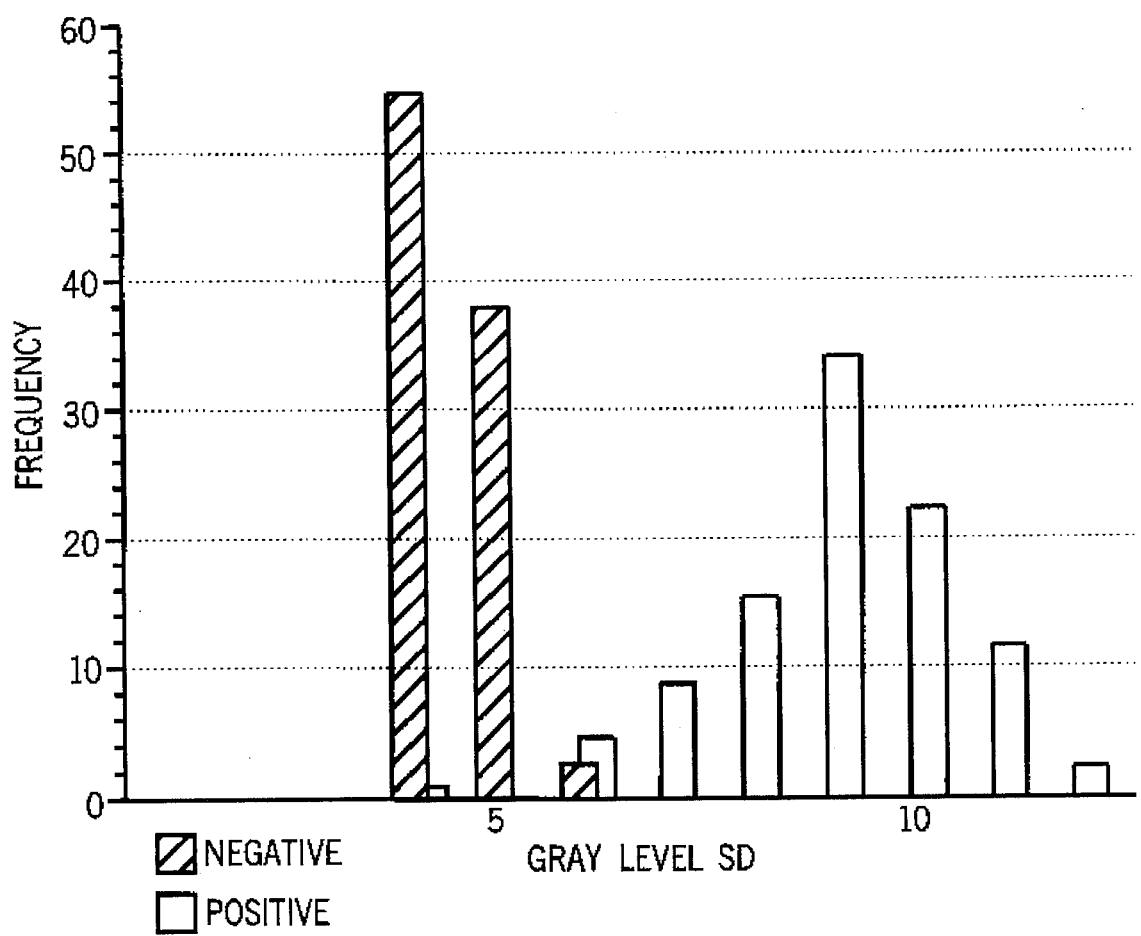

QUANTATIVE AGGLUTINATION REACTION ANALYSIS METHOD

BACKGROUND OF THE INVENTION

Embodiments described herein relate generally to a method of analysis and relate more specifically to a method for analyzing or reading an agglutination reaction.

Analysis methods are available to analyze a number of reactions, such as immunochemical reactions and the like. One such reaction is an agglutination reaction. For example, in an agglutination reaction, elements are mixed together on a tray such that, if the reaction is "positive," the elements group, collect or clump together, and if the reaction is "negative," the elements do not clump together. Classification of the agglutination reaction may be in two, i.e. positive or negative, or more, i.e. negative, positive, borderline, etc., classes. The classes may be dependent upon the strength or degree of clumping of the elements mixed together. The degree of clumping may be indicative of a property of one of the elements. In one instance, this property may be the presence of an item of interest, such as an antibody, a protein and the like, in an element.

Once the agglutination reaction takes place, the results of the reaction should be read or should be analyzed in order to determine, for instance, whether the reaction is positive or negative. One way of reading this reaction is for an operator to look at the tray on which the reaction took place. The operator, upon looking at the tray, decides, based on his own interpretation of what he sees, whether the reaction is positive or negative. The operator reports his read of the reaction to others, such as a doctor and the like, who may make a decision of treatment based on the report from the operator.

By reading the agglutination reaction in this manner, a number of problems may occur. Because the operator uses his own interpretation of what he sees, the level of skill of the operator may effect the reported results of the reaction. For instance, an operator who has many years of training and experience in reading an agglutination reaction may make a more accurate read of the agglutination reaction than an operator who does not have as much training and experience. This possible difference in readings of a given reaction is of interest given that a doctor's treatment decision may be based on that reading.

In an effort to reduce the likelihood of possibly adverse effects caused by an operator's reading of an agglutination reaction, automated methods of reading reactions have been developed. While these methods may provide advantages over an operator's read of a reaction, there is always room for improvement.

For example, one automated method of reading an agglutination reaction detects light sent from a tray on which the agglutination reaction takes place. The intensity of the light is measured. The reaction is determined to be positive, negative or not identified, i.e. placed into one of two or three classes. However, variations or changes in the light detected may adversely effect the reading of the reaction. Additionally, increased detail or the ability to place a given reaction into multiple classes may be difficult. Further, relations between two classes of a given reaction may not be easily identified.

Given these considerations, it is desirable to provide an improved analysis method for reading a reaction and specifically for reading an agglutination reaction.

SUMMARY OF THE INVENTION

Embodiments described herein provide methods of analysis of a reaction, such as an agglutination reaction producing an agglutination pattern, and the like. In one method, an image of the agglutination pattern is captured. The image captured is digitized to form a digital image comprising a pixel. Roughness is measured, reflecting pixel local environment, at each pixel comprising a region of interest of the digital image of the agglutination pattern. At least one of classification and quantification of the image captured of the agglutination pattern is performed based on the measured roughness.

In another embodiment, an image of the agglutination pattern is captured. The image captured is digitized to form a digital image comprising a pixel. Roughness is derived using a shared weights neural network approach, the roughness reflecting pixel local environment at each pixel comprising a region of interest of the digital image of the agglutination pattern. At least one of classification and quantification of the image captured of the agglutination pattern is performed based on the derived roughness.

In a further embodiment, an image of the agglutination pattern is captured. The image captured is digitized to form a digital image comprising a pixel. A feature is derived using a shared weights neural network approach, the feature reflecting pixel local environment at each pixel comprising a region of interest of the digital image of the agglutination pattern. At least one of classification and quantification of the image captured of the agglutination pattern is performed based on the derived feature.

BRIEF DESCRIPTION OF THE DRAWINGS

FIG. 6 is a plot derived from a conventional analysis method yielding an overlap between positive and negative reactions, thereby possibly complicating acceptable classification.

DETAILED DESCRIPTION OF PREFERRED EMBODIMENTS

Embodiments described herein generally relate to a method of analyzing a chemical reaction. For the sake of clarity, an exemplary embodiment of the method will be discussed. This exemplary embodiment is used to analyze an agglutination reaction, such as those found in certain immunoassays. While this exemplary embodiment and use will be discussed in detail, it is to be recognized that other embodiments and uses of the method are also possible. For instance, elements of one method may be combined with elements of another method to produce yet an additional method. This additional method may be employed in the same use as the other methods or in a different use. Also, the steps comprising a specific method may be performed in any suitable order.

Figure 1:
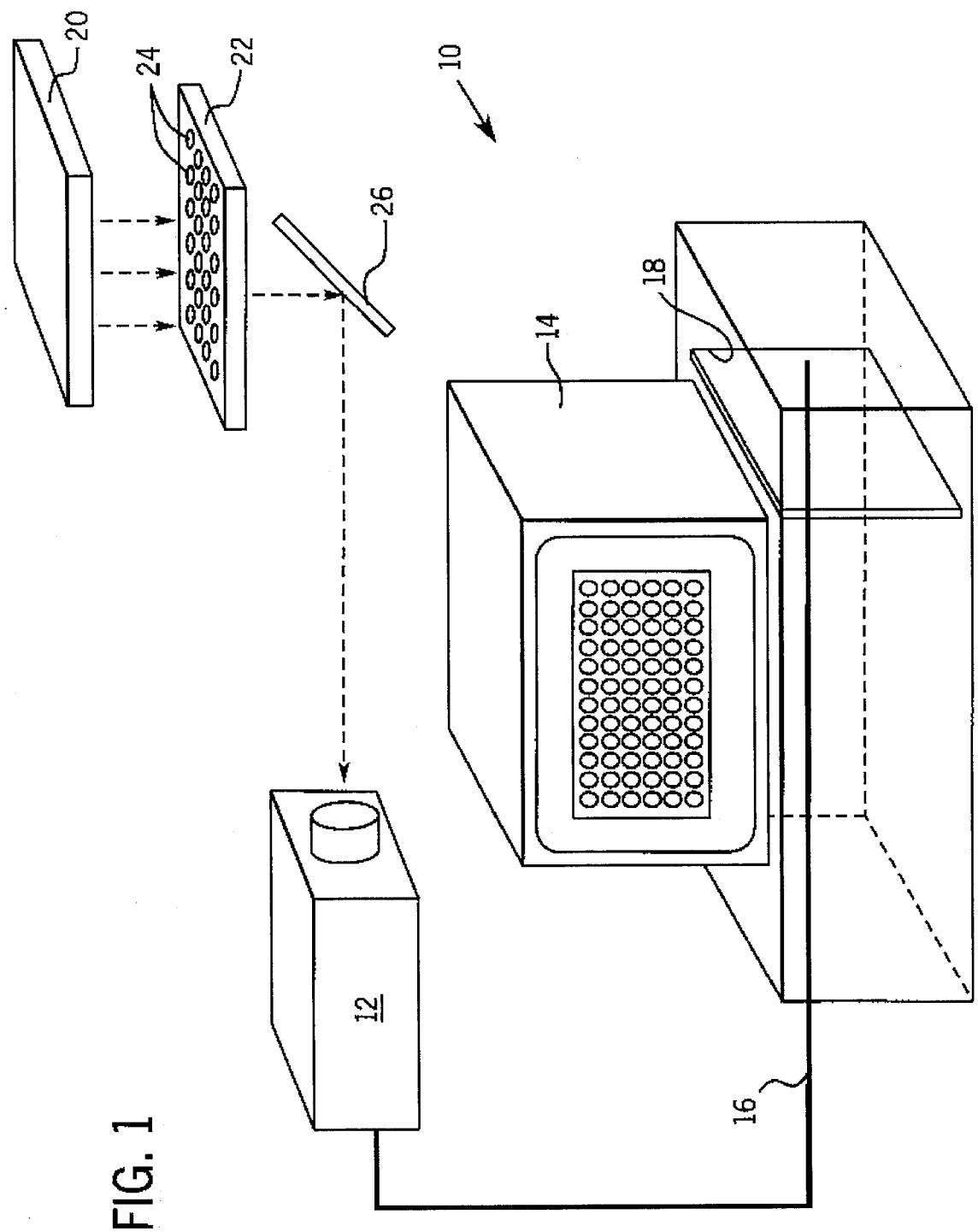
FIG. 1 is a generic, diagrammatic illustration of an analysis system for use with the analysis method described herein.

The exemplary embodiment of the method may be performed with an analysis system 10, such as that illustrated generically in FIG. 1. The analysis system 10 generally comprises an electronic image acquisition device 12, such as a camera and the like, and a computer 14 electrically connected with the image acquisition device 12 by a conductor 16. The computer 14, in one embodiment, contains image acquisition hardware such as a frame grabber 18. In another embodiment, the computer 14 is an IBM AT personal computer, and the image acquisition hardware is a Quantex QX-7 Image Processing System (Quantex Corporation, Sunnyvale, Calif.). The computer 14 contains a memory, such as a RAM, a ROM, an EPROM, a SRAM and the like, including and running appropriate routines such that the computer 14 controls and monitors all relevant operations of the analysis system 10.

In an exemplary embodiment of the analysis system 10, the image acquisition device 12 is a charge-coupled device (CCD) camera with a resolution of at least about 320×240 or about 256×256 pixels. One applicable CCD camera is a PULNiX TM-840 (PULNiX America, Inc., Sunnyvale, Calif.) having a Nikon 60 mm F2.8 lens. A microscope and camera combination may be used in lieu of the camera and lens combination.

The analysis system 10 can include a source 20 of electromagnetic radiation. The source 20 of electromagnetic radiation illuminates a reaction tray 22 containing one or more reaction cells 24. Electromagnetic radiation transmitted from the reaction cells 24 in the reaction tray 22 is sent to the image acquisition device 12. If necessary, a mirror 26 and/or other electromagnetic radiation-directing components may be provided in the path of electromagnetic radiation between the reaction tray 22 and the image acquisition device 12.

An electronic signal representing an image of a given reaction cell 24 is produced by the image acquisition device 12. It may be desirable to position the source 20 of electromagnetic radiation adjacent open ends of the reaction cells 24, i.e. "above" the reaction tray 22 as viewed in FIG. 1, and acquire the image of a given reaction cell 24 from a side of the reaction tray 22 opposite to the side thereof adjacent the open ends of the reaction cells 24, i.e. "below" the reaction tray 22 as viewed in FIG. 1. By so positioning the image acquisition device 12 with respect to the reaction tray 22, it is possible to reduce image compromising effects, such as that caused by a meniscus curve formed in the given reaction cell 24. In other embodiments, depending upon the configuration and construction of the reaction tray 22, the image acquisition device 12 and the like, placement of the image acquisition device 12 and/or the source 20 of electromagnetic radiation may be altered to accommodate requirements of image acquisition.

The image acquisition device 12 produces an electronic signal responsive to the electromagnetic radiation received from the reaction tray 22. The electronic signal is transmitted from the image acquisition device 12 along the conductor 16 to the image acquisition hardware, i.e. frame grabber 22. The frame grabber 22 converts the electronic signal from the image acquisition device 12 to a digital image data format suitable for storage, processing, and display by the computer 14. The digital image information generally includes intensity values (or gray level) for a set of image elements (pixels) organized in a two-dimensional array. An individual pixel may be specified with coordinates i,j indicating that the pixel is located at row i and column j in the image.

Processing of the digital image data by the computer 14 produces a quantitative indication of an extent of agglutination present in the given reaction cell 24. This processing generally comprises extraction and quantification of local intensity information in the digital image data. The term "local" indicates that information is derived from a relationship between intensity of a given pixel and its "close," e.g. a specified number of pixels away (3, 5, 7 . . . ), neighbors. A feature concerning the digital image data is measured or derived. A feature is generally understood to mean a group of related pixels, the relation between/among the pixels being suitable for use in classification, quantification and the like. Examples of a feature include: roughness, entropy, statistical measures (e.g. standard deviation), a converted image based on local intensity variation, intensity degree, texture, etc.

One example of local intensity information is defined as roughness, i.e. a measurement of local intensity variation. The value of the roughness at a certain location i,j (designated $R_{i,j}$) is expressed as:

$$R_{i,j} = \sum_{m,n \in A} |P_{i,j} - N_{m,n}|/C_s$$

where $P_{i,j}$ and $N_{m,n}$ are gray level values at locations i,j and m,n, respectively A is an area surrounding location i,j and $C_s$ is a normalization constant for the area A.

In a specific embodiment, a weight of $N_{m,n}$ may be selected based on a relation of $P_{i,j}$ and $N_{m,n}$. In one embodiment, the area A consists of a square kernel about 5 pixels wide centered on location i,j. An example of a computer software routine that may be used to calculate roughness values for digital image data is presented at Appendix A which appears at the end of this description and before the claims.

Another form of local intensity information is derived using a shared weights neural network approach. The neural network generalizes local intensity information derivation to a feature determined by the network, i.e. the neural network chooses its own feature of interest. As described in "ANSim USER MANUAL," the disclosure of which is incorporated herein in its entirety and which is available from Science Applications International Corporation, San Diego, Calif., a mask calculates a weighted sum of intensity levels of pixels near a particular pixel. The resulting weighted sum values are input values to a neural network that modifies weights of the mask. An example of computer software that may be used to execute the shared weights neural network procedure is ANSim, available from Science Applications International Corporation, San Diego, Calif. As in the roughness calculation, information is derived from local intensity values throughout the digital image data.

In some cases it may be desirable to perform image processing procedures prior to extraction of local intensity information. For example, in one embodiment of the analysis, multiple images of the same reaction cell 24 may be acquired and an average of those multiple images produced. A filtering algorithm may also be employed to reduce adverse artifacts resulting from a digitization process.

Extracted local intensity information may be used to quantify or to classify strength or intensity of the agglutination reaction. Various methods exist to perform this quantification. A mean roughness value for a region of interest, e.g. an area surrounding approximately a center of a given reaction cell 24, may be indicative of the agglutination reaction. Alternatively, measures of a variation in local intensity variation measurements, such as standard deviation of roughness, may be used. If the shared weights neural network approach were used, then the neural network itself may yield a numerical or discrete classification output of the analysis.

To further describe exemplary embodiments of the method, the following examples of application of the method are given. It is to be noted that these examples are provided for illustrative purposes and are not intended to limit the method.

EXAMPLE 1

In a first exemplary application, an embodiment of the method may be used to quantify an amount of agglutination in an immunoassay which detects antibodies to the hepatitis C virus (HCV). The materials are available in a HCV PHA kit available from Dainabot, located in Tokyo, Japan. Varying agglutination reaction responses are produced in accordance with the following procedure:

1. about 75 μl of specimen dilution buffer is added to the 1st well of four rows in a 96-well HCV PHA kit accessory plate.
2. about 25 μl of specimen dilution buffer is added to the next 10 wells in the four rows of the plate.
3. about 25 μl of a serum sample known to contain HCV antibodies (a "positive control") is added to the first well of two of the four rows in the plate and is mixed with the about 75 μl of dilution buffer. Similarly, about 25 μl of a serum sample known to lack HCV antibodies (a "negative control") is added to the first well of the other two of the four rows in the plate and is mixed with the about 75 μl of dilution buffer. The resulting dilution ratio in these first wells is about 1:4.
4. For each row, about 25 μl of the diluted sample is removed from the first well and is mixed with the about 25 μl of dilution buffer in the second well. The resulting dilution ratio in these second wells is about 1:8.
5. For the remaining 8 wells in each row, about 25 μl of sample in the preceding well is removed and is mixed with the about 25 μl of dilution buffer in the well.
6. Further similar dilution steps are performed to yield a range of dilution ratios of about $1:2^4$ to about $1:2^{20}$ for the positive controls and about $1:2^4$ to about $1:2^{12}$ for the negative controls.
7. about 25 μl of a suspension of fixed human erythrocytes (duracytes) coated with rHCV antigens (HCV PHA duracytes available from Dainabot, Tokyo, Japan) is added into all wells, is mixed gently, and is allowed to incubate at room temperature for about 2 hours.

Agglutination response in the various reaction cells 24 is judged by eye and recorded. Then, the reaction cells 24 are analyzed using an exemplary embodiment of the method as follows:

1. Digital images of the reaction cells 24 are acquired using an analysis system 10, such as that illustrated in FIG. 1.
2. Roughness is measured for all pixels in a substantially circular area with a radius of about 10 pixels centered on the approximate center of each reaction cell 24. The roughness is measured using a 5×5 kernel.
3. Mean roughness values for each reaction cell are calculated.

Figure 2:
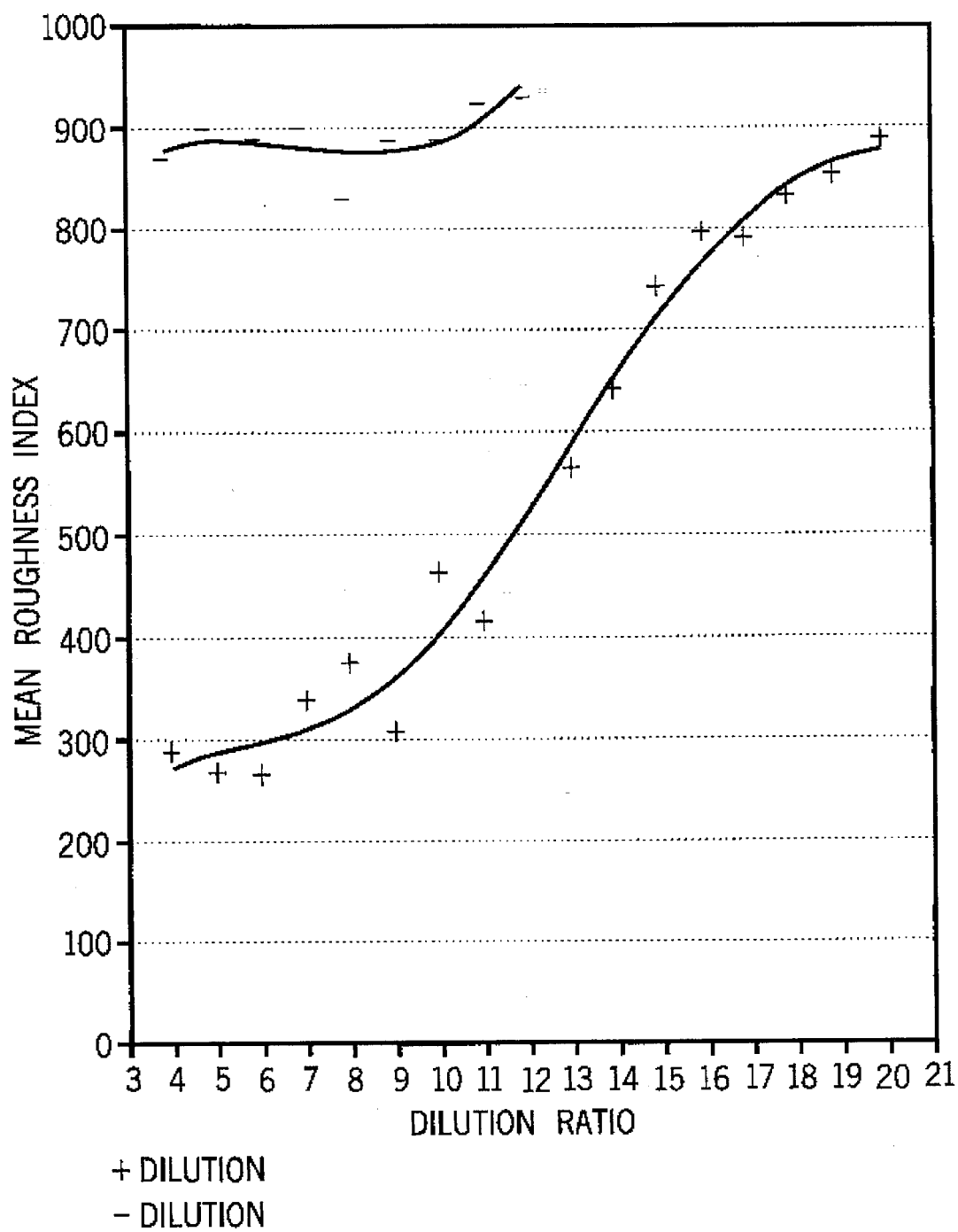
FIG. 2 is a plot of a mean of mean roughness values for reaction cells versus dilution ratios for four repetitions of an example described herein.

A plot of a mean of the mean roughness values for each of the reaction cells 24 versus dilution ratios for four repetitions of the above-described example is presented in FIG. 2. For positive control dilution samples an overall correlation coefficient is 0.95. In the dilution ratio range of about $1:2^{13}$ to about $1:2^{20}$, and this range may be problematic for visual scoring, the response curve is substantially monotonic. Negative control dilution samples yielded values within a relatively narrow range substantially similar to that of the highest levels of dilution of positive controls. This procedure may also be used, with suitable modifications, i.e. using standard deviation of roughness instead of mean roughness, to assess quality of agglutination reagents, such as coated fixed human erythrocytes, by quantitatively analyzing their response to varying concentrations of the analyte for which they are produced.

EXAMPLE 2

An embodiment of the method described herein may be used to measure an amount of alpha fetal protein (AFP) in a serum sample. An agglutination reaction is performed on a device substantially similar to that described in U.S. Pat. No. 5,209,904, "Agglutination Reaction Device Utilizing Selectively Impregnated Porous Material," issued May 11, 1993. That patent is assigned to the assignee of the present invention and the disclosure thereof is incorporated herein by reference. Duracytes in the agglutination reaction device in this example are coated with antibodies that bind to AFP, therefore agglutinating in the presence of AFP.

Measurement of AFP concentration is performed for samples of varying AFP concentrations (e.g. about 0, 2, 10 and 50 ng/ml) and various sample volumes (between about 8 μl and about 12 μl) as follows:

1. Serum samples with varying AFP concentrations are mixed with about 10 μl of an approximately 10% suspension of duracytes coated with anti-AFP antibodies at a level of about 100 μg per ml of cells. The mixture is analyzed in an analysis system with a method similar to that described in example 3 of US Pat. No. 5,248,479, "Agglutination Reaction Device Having Geometrically Modified Chambers," issued Sep. 28, 1993. That patent is also assigned to the assignee of the present invention and the disclosure thereof is incorporated herein by this reference.
2. A digital image is acquired for each agglutination response. The digital image is acquired by summing 8 sequential images and dividing by 8.

3. The digital image is filtered using a median filter with a 5×5 kernel to reduce artifacts from the digitization. Artifacts are image distortions which may arise due to acquisition of a complete set of pixels, viz. a frame, by the image acquisition system in two scans, i.e. fields. Variations between gray level values of pixels may be deemed as artifacts because of their acquisition in different fields rather than because of actual variations in brightness or intensity between their positions. Reduction or removal of these artifacts may be performed by using a median filter.

4. Roughness for each pixel is calculated using a 5×5 roughness kernel for a substantially rectangular region of interest (e.g. 398×66 pixels).

Figure 3:
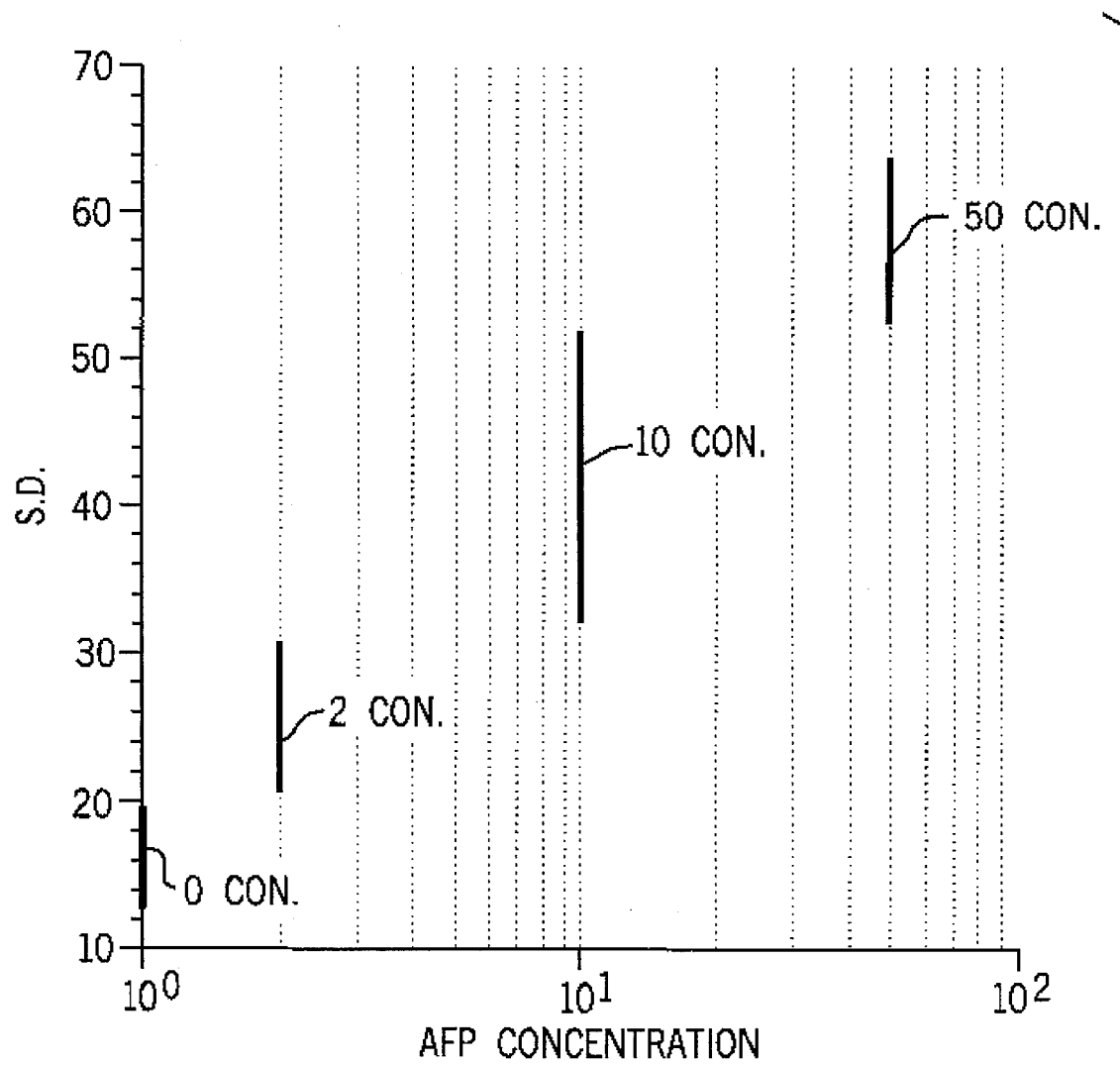
FIG. 3 is a plot of standard deviation of roughness versus sample AFP concentration for 400 AFP samples.

5. A standard deviation of the roughness values in the region of interest is calculated. A plot of the standard deviation of the roughness versus an item of interest, viz. the sample AFP concentration, demonstrating the correlation between the two, is shown in FIG. 3 for a total of 400 AFP samples.

EXAMPLE 3

The method described herein may be used, for example, to automatically classify agglutination reactions in a screening test for drugs of abuse. Panel tests for abused drugs using antifluorescein-coated fixed human erythrocytes are performed in a manner similar to Example 10 of U.S. Pat. No. 5,270,166, "Immunoassays Employing Generic Anti-hapten Antibodies and Materials for use Therein," issued 14 Dec. 1993. That patent is owned by the assignee of the present invention and the disclosure thereof is incorporated herein by reference.

Figure 4:
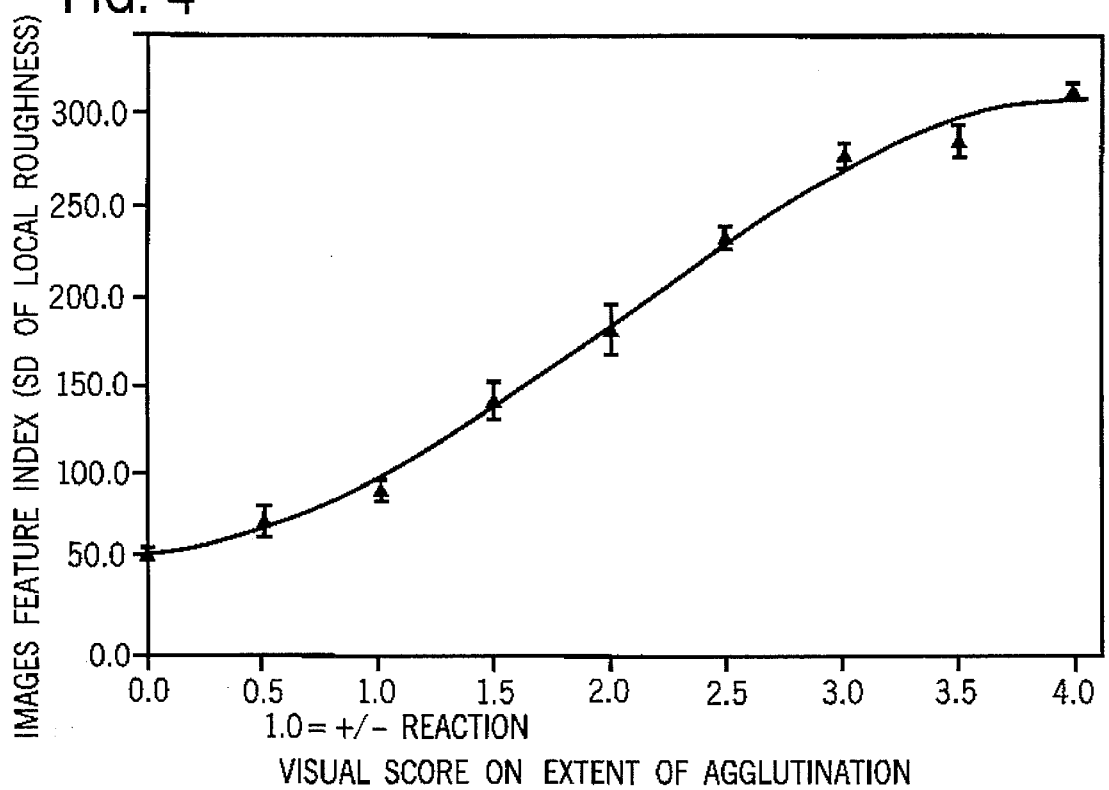
FIG. 4 is a plot of standard deviation of roughness values versus visual agglutination score.

1. Extent of agglutination is determined visually and scored on a scale of 0.0 (no agglutination) to 4.0 (maximum agglutination).
2. Digital images are acquired of the reaction chambers of the agglutination reaction device.
3. Digital images are filtered with a median filter with a 5×5 kernel.
4. Roughness values are calculated for the resulting digital images with a 7×7 kernel.
5. Standard deviation of roughness in a region of interest is calculated and used as an indicator of the extent of agglutination. A plot of the standard deviation of the roughness values versus the visual agglutination score is presented in FIG. 4, demonstrating that the local intensity information (in the form of standard deviation of roughness) quantifies the extent of agglutination and correlates to features of visual information.

EXAMPLE 4

Figure 5:
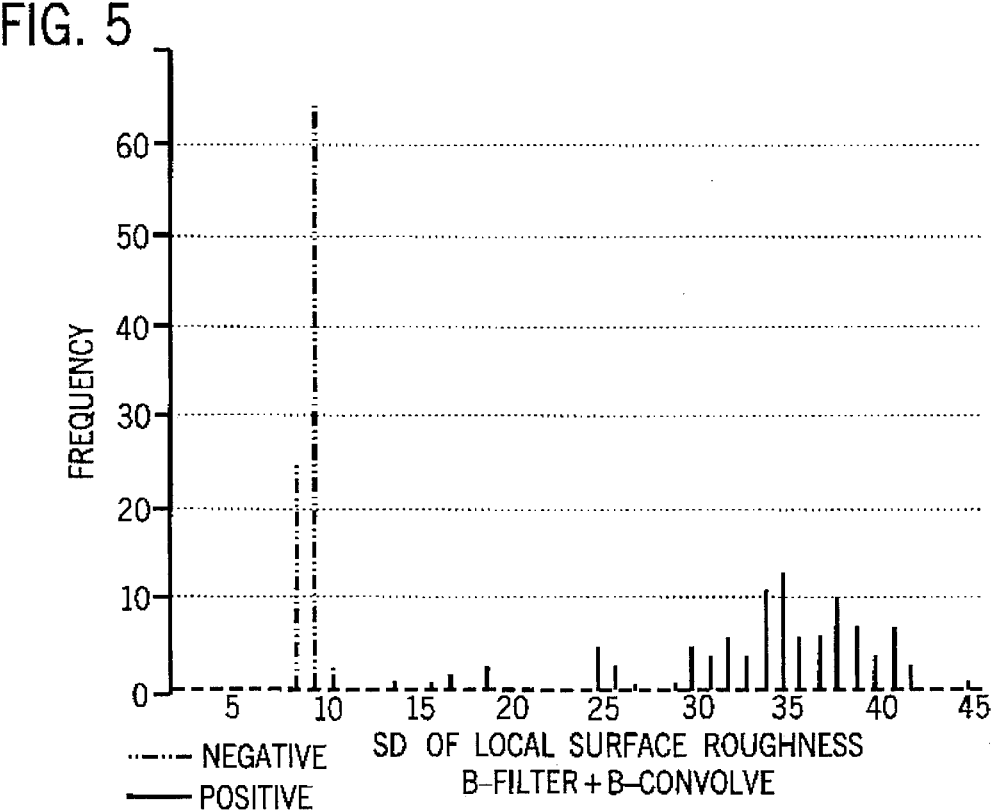
FIG. 5 is a plot of standard deviation of roughness values throughout a region of interest.

An embodiment of the method described herein may be used for blood typing analysis in an agglutination reaction device similar to that described in U.S. Pat. No. 5,209,904, "Agglutination Reaction Device Utilizing Selectively Impregnated Porous Material," issued May 11, 1993. That patent is assigned to the assignee of the present invention and the disclosure thereof is incorporated herein by reference. Example 2 of this patent describes an agglutination assay used to determine blood type. The analysis of this agglutination may be executed with an embodiment of the method described herein as follows:

1. Electronic images are acquired of the reaction chamber of the agglutination reaction device. Typically 8 images are averaged in this acquisition step by summing and dividing by 8.
2. An average image of a particular reaction chamber is filtered with a median filter with a 5×5 kernel.
3. Roughness values of each pixel in the image are calculated with a 5×5 kernel.
4. Standard deviation of the roughness values throughout a region of interest is calculated. This value is indicative of the amount of aggregation and, as shown in FIG. 5, may be used to distinguish positive (agglutinated) from negative (non-agglutinated) reactions.

This result may be contrasted with a conventional method of judging which relies only on global image information rather than local intensity information. This conventional method consists of calculating a standard deviation of gray level values for all pixels in the image:

$$\sigma = \sqrt{\frac{\Sigma(P_{i,j} - \mu)^2}{n-1}}$$

where $\sigma$ is the standard deviation $P_{i,j}$ is the gray level value at location i,j $\mu$ is the average gray level value in the image and n is the number of pixels in the image As shown in FIG. 6, the conventional method yields an overlap between positive and negative reactions, preventing satisfactory classification. The use of local intensity information as described in this example overcomes this limitation.

EXAMPLE 5

Another embodiment of the method described herein may be used for analysis of the agglutination reaction images obtained in Example 4. This embodiment of the method uses a shared weights back propagation method, such as that described in the "ANSim USER MANUAL," available from Science Applications International Corporation, San Diego, Calif. The method comprises the following steps:

1. Digital images of agglutination reactions are reduced to 199×66 pixel images with 2:1 averaging of rows.
2. Pixel intensity levels are linearly scaled so that the maximum pixel value is 64.
3. Three 64×64 non-overlapping subimages are extracted from a region of interest in the agglutination image.
4. A shared weights back propagation net routine of ANSim version 2.30 (Science Applications International Corporation, San Diego, Calif.) is applied, with four 3×3 receptive fields. The neural net is "trained" for 10000 cycles on 97 training images and then applied to 97 test images. This application yielded 91 correct classifications and 6 classification errors when compared to visual scoring of the images.

EXAMPLE 6

A further embodiment of the method described herein may be used for automated analyses of agglutination reactions for blood typing. The reactions may be similar to those described in U.S. Pat. No. 5,283,178, "Method of Forming Agglutinates in Blood Samples," issued 1 Feb. 1994. That patent is assigned to the assignee of the present case and the disclosure thereof is incorporated herein by reference. The reactions may be analyzed as follows:

1. A digital image is acquired for each reaction cell.
2. All pixels within a region of interest are classified as "clear," "dark," or "rough" in accordance with the following criteria:
   A "clear" pixel has a gray level higher than a particular threshold (such as about 200, for example).
   A "dark" pixel has a gray level lower than a particular threshold (such as about 20, for example).
   A "rough" pixel has a gray level between the two thresholds specified above.
3. All rough pixels have their local roughness calculated with a 5×5 kernel.
4. The reaction is classified in accordance with the following criteria (the steps may be executed sequentially):
   If a fraction of a total area that is rough is greater than about 99% and a standard deviation of an intensity of the total area is less than about 30, the reaction is 'S+' (or 'sticky positive').
   If a fraction of a total area that is rough is greater than about 95% and a standard deviation of an intensity of the total area is less than about 16, the reaction is 'S+.'
   If a fraction of a total area that is dark is greater than about 20%, the reaction is 'O' (or 'negative').
   If the standard deviation of the roughness of the rough area is less than about 9 and the maximum roughness in the rough area is greater than or equal to about 100, the reaction cell is noted as containing an air bubble and the reaction is 'O.'
   If the fraction of the total area that is rough is greater than about 90% and less than about 96% and the standard deviation of the roughness of the rough area is greater than about ten and the fraction of the total area that is clear is less than about 3%, the reaction is 'W+' (or 'weak positive').
   If the mean intensity of the entire area is between about 130 and about 150, and the standard deviation of the intensity of the entire area is between about 81 and about 99, and the standard deviation of the roughness of the rough area is between about 61 and about 78, and the fraction of the total area that is rough is between about 60% and about 74%, and the fraction of the total area that is dark is between about 3% and about 7%, and the number of dark clusters is between about 5 and about 12, and the fraction of the total area that is clear is between about 19% and about 35%, the reaction is 'R+' (or 'rough positive').
   If the fraction of the total area that is clear is greater than 0.1%, the reaction is '+' (or 'positive').
   If the standard deviation of the roughness of the rough area is greater than about 9, the reaction is '+.'
   If the standard deviation of the roughness of the rough area is less than or equal to about 9 and the number of dark clusters is greater than or equal to about 20, the reaction is '+.'
   If the standard deviation of the roughness of the rough area is less than about 9, the reaction is 'O.'

The numerical values used as pixel thresholds and classification criteria may be adjusted for particular analysis conditions. In general, the values are determined from information acquired from 'negative' control samples.

The results of using this embodiment of the method are displayed in the following table, as well as results using intensity information in a conventional classification scheme described in U.S. Pat. No. 5,283,178, "Method of Forming Agglutinates in Blood Samples," issued 1 Feb. 1994. That patent is assigned to the assignee of the present invention and the entire disclosure thereof is incorporated herein by reference.

A correct classification is defined as properly automatically classifying a reaction as positive (including 'S+', 'R+', 'W+', or '+' classifications) or negative (an 'O' classification), measured against visual classification. It is important to recognize that the disclosed embodiments of the method achieve substantially more accurate classification of sticky positive (S+) reactions than results from intensity feature classification methods.

| | Classification by Visual Scoring | | | | | | |
|---|---|---|---|---|---|---|---|
| | O | Granular (+) | S+ | W+ | R+ | + | Inconclusive |
| Correct classifications using disclosed embodiment (1040 samples) | 649/651 (100% correct, with 2 air bubble detections) | 19/21 (90.5%) | 44/44 (100%) | 22/22 (100%) | 17/17 (100%) | 277/277 (100%) | 8 |
| Correct classifications using intensity feature analysis method (1129 samples) | 705/705 (100%) | 1/22 (4.5%) | 15/48 (31.3%) | 5/27 (18.5%) | 22/22 (100%) | 297/297 (100%) | 8 |

By performing analysis of a reaction according to the method described herein, it is possible to realize desired benefits. For instance, information can be obtained regarding precipitate particle nature. Differentiation between agglutinated particles and accumulations of non-agglutinated particles is possible. Insight into a three dimensional structure of agglutinates may be had. Furthermore, it is possible to differentiate among sizes of agglutinated particles.

APPENDIX A

```
/* Abbott Laboratories
     Local Surface Roughness.
   Algorithm Developer: Yongli Xiong.
     Generate date: April 12, 1989.
   Compiler: TITAN C 1.0.
     Version: 2.0.
   ***********************************************************
     Input format: Binary, unsigned char, 16 bytes header.
     Input  range: 0 to 255.
     Kernel size : odd, > 1.
   ---------------------------------------------------------------
   Veriable notes
     Image dimension : ROW, COL.
   Total of pixels : TOTAL.
     Shifted dimension: SFTROW, SFTCOL.
   File header : *size.
     Dimension counter: row, col.
   Kernal size : ftsize.
     Shift pixel # : shift.
   Shifted file size: SFTTOTAL.
     File handle : fhd.
   Counter: l, m, dump.
   */ include <stdio.h>
   #include <malloc.h>
   #include <sys/types.h>
   #include <fcntl.h>              /* for open */
   #include <sys/file.h>           /* for open */
   #include <sys/stat.h>
   #include <search.h>
   #include <math.h>
```

```
main(argc, argv)

int argc;
char *argv[];

{
    long row, col, l, m, ROW, COL, TOTAL, SFTTOTAL,
SFTCOL, SFTROW, temp;
    int fhd, ftsize, shift, dump, x1, x2;
    unsigned char *size, *image;
    int *imgdata;
    float min, max, sum, mean, mom2, sd;

if(argc != 4)
        {
        printf("\nUSAGE: %s input-file-name output-file-name
kernal-size\n", argv[0]); }
        else
        {
            if((fhd = open(argv[1], O_RDONLY)) == -1)
            {
            perror("open failed on input file");
            exit(0);
            }
            size = (unsigned char *)malloc((unsigned)16);
/* find size */
            read(fhd, size, 16);
            COL = (int)(*size) + (int)(*(size+1)) * 256;
            ROW = (int)*(size+2) + (int)(*(size+3)) * 256;
            TOTAL = ROW * COL;
            ftsize = atoi(argv[3]);
            SFTCOL = COL + ftsize - 1;
            SFTROW = ROW + ftsize - 1;
            shift = (ftsize -1)/2;
```

```
/* allocated memory */
        SFTTOTAL = TOTAL + 2 * shift * (SFTROW + COL);
        image = (unsigned char
*)malloc((unsigned)SFTTOTAL);
        imgdata = (int
*)malloc((unsigned)TOTAL*sizeof(int));
        if ((image && imgdata) == NULL) {
            printf("Insufficient memory available. \n");
            close(fhd);
            exit(0);   }

/* read data */
        l=read(fhd, image, (unsigned)TOTAL);
        close(fhd);

/* shift array */
        for (row = ROW-1; row >= 0; row--)
            for (col = COL-1; col >= 0; col--)  {
        *(image + (row + shift) * SFTCOL + col + shift) =
*(image + row *
COL + col);
            }
/* fill edge */
        for (row = 0; row < shift; row++)
            for ( col = shift; col < (COL + shift);
col++)  {
                *(image + row * SFTCOL + col) = *(image +
shift * SFTCOL +
col);
                *(image+ (row+ROW+shift) * SFTCOL + col) =
*(image+(ROW-1+shift) * SFTCOL+col);
            }
        for(col = 0; col < shift; col++)
            for(row = 0; row < SFTROW ; row++)   {
```

```
                            *(image + row * SFTCOL + col) = *(image +
            row * SFTCOL +
            shift);
                            *(image+row * SFTCOL + COL+shift +col) =
 5          *(image + row *
            SFTCOL +COL-1+shift);
                            }

/* compute the roughness */
10                          for(row = shift; row < ROW + shift; row++)
                            for(col = shift; col < COL + shift; col++)
                            {
                                    dump = 0;
                                    temp = row * SFTCOL + col;
15                                  for(l = row - shift; l < row + shift +
            1; l++)
                                    for(m = col - shift; m < col + shift +
            1; m++)
                                            {
20                                          dump=(dump+abs((*(image +
            temp))-(*(image+l*SFTCOL+m))));
                                            }
                                    *(imgdata + (row-shift) * COL + (col-
            shift)) = dump;
25                                  if(dump > 255) dump = 255;
                                    *(image+(row-shift) * COL+(col-
            shift))=(unsigned
            char)dump;
                            }
30          /* computer the sd */
                    sum = 0.0;
                    min = *imgdata;
                    max = *imgdata;
                    mom2 = 0.0;
35                  dump = 0;
```

```
        x1 = 15 + shift;
        x2 = 265 - shift;
        for(row = 30; row < 350; row ++)    {
            temp = row * COL;
            if(row <= 210) {
                if(fmod((double)row, 2.0) != 0.0)   {
                    x1 = (x1 + 1);
                    x2 = (x2 - 1);
                }
            }
            for(col = x1; col < x2; col++)      {
                sum = (sum + (*(imgdata+temp+col)));
                if(max < (*(imgdata+temp+col))) max = *(imgdata+temp+col);
                if(min > (*(imgdata+temp+col))) min = *(imgdata+temp+col);
                dump = (dump + 1);
            }
        }
        mean = sum / dump;
        x1 = 15 + shift;
        x2 = 265 - shift;
        for(row = 30; row < 350; row++) {
            temp = row * COL;
            if(row <= 210) {
                if(fmod((double)row, 2.0) != 0.0)   {
                    x1 = (x1 + 1);
                    x2 = (x2 - 1);
                }
            }
            for(col = x1; col < x2; col++)      {
                mom2 = (mom2 +
    pow(((*(imgdata+temp+col)) - mean),
    2.0));
            }
```

```
                }
                sd = (float)sqrt((double)(mom2/dump));
/* write file */

5      if((fhd=open(argv[2],O_RDWR|O_CREAT|O_EXCL,S_IREAD
        |S_IWRITE))==
         -1)
                {

10      if((fhd=open(argv[2],O_RDWR|O_TRUNC,S_IREAD|S_IWRITE)) == -
        1)    {
                        perror("open failed on output file");
                        exit(0);   }
                }
15              write(fhd, size, 16);
                l = write(fhd, image, (unsigned)TOTAL);
                close(fhd);
                free(image);
                free(size);
20              printf("%s %6.2f %6.2f %6.2f %f\n", argv[2], min,
        mean, max, sd);
            }
        }

25      ================================================================
```

What is claimed is:

1. A method of analysis of an agglutination reaction producing an agglutination pattern, the analysis method comprising the steps of:
   (a) photoelectrically capturing an image of the agglutination pattern;
   (b) digitizing the image captured to form a digital image comprising a pixel;
   (c) measuring roughness, reflecting pixel local environment, at each pixel comprising a region of interest of the digital image of the agglutination pattern; and
   (d) performing at least one of classification and quantification of the image captured of the agglutination pattern based on the measured roughness.

2. A method of analysis as defined in claim 1 further comprising the step of:
   (e) reducing an artifact generated during the digitizing step (b).

3. A method of analysis as defined in claim 1 further comprising the step of:
   (e) calculating at least one of standard deviation and mean of the measured roughness.

4. A method of analysis as defined in claim 3 further comprising the step of:
   (f) correlating the standard deviation of the measured roughness with a concentration of an item of interest.

5. A method of analysis as defined in claim 3 further comprising the step of:
   (f) correlating the standard deviation of the measured roughness with a quantification of agglutination.

6. A method of analysis as defined in claim 1 wherein step (d) comprises performing at least one of classification and quantification of the image captured of the agglutination pattern based on statistics of the measured roughness.

7. A method of analysis as defined in claim 1 further comprising the steps of:
   (e) calculating a mean of measured roughness; and
   (f) correlating the mean of measured roughness with a concentration of an item of interest.

8. A method of analysis as defined in claim 3 further comprising the step of:
   (f) calculating a mean of measured roughness; and
   (g) correlating the mean of measured roughness with a quantification of agglutination.

9. A method of analysis of an agglutination reaction producing an agglutination pattern, the analysis method comprising the steps of:
   (a) photoelectrically capturing an image of the agglutination pattern;
   (b) digitizing the image captured to form a digital image comprising a pixel;
   (c) deriving roughness using a shared weights neural network approach, the roughness reflecting pixel local environment at each pixel comprising a region of interest of the digital image of the agglutination pattern; and
   (d) performing at least one of classification and quantification of the image captured of the agglutination pattern based on the derived roughness.

10. A method of analysis as defined in claim 9 further comprising the step of:
    (e) reducing an artifact generated during the digitizing step (b).

11. A method of analysis of an agglutination reaction producing an agglutination pattern, the analysis method comprising the steps of:
    (a) photoelectrically capturing an image of the agglutination pattern;
    (b) digitizing the image captured to form a digital image comprising a pixel;
    (c) deriving a feature using a shared weights neural network approach, the feature reflecting pixel local environment at each pixel comprising a region of interest of the digital image of the agglutination pattern; and
    (d) performing at least one of classification and quantification of the image captured of the agglutination pattern based on the derived feature.

12. A method of analysis as defined in claim 11 further comprising the step of:
    (e) reducing an artifact generated during the digitizing step (b).

* * * * *

UNITED STATES PATENT AND TRADEMARK OFFICE
CERTIFICATE OF CORRECTION

PATENT NO. : 5,541,417
DATED : August 20, 1996
INVENTOR(S) : Breivogel et al.

It is certified that error appears in the above-identified patent and that said Letters Patent is hereby corrected as shown below:

<u>Title page,</u>
Item [75], delete "Matthew J. Price" and replace with -- Matthew J. Prince --.

Signed and Sealed this

First Day of April, 2003

JAMES E. ROGAN
*Director of the United States Patent and Trademark Office*